(12) United States Patent
Sakakura et al.

(10) Patent No.: US 10,578,693 B2
(45) Date of Patent: Mar. 3, 2020

(54) MAGNETIC RESONANCE IMAGING APPARATUS AND GRADIENT COIL

(71) Applicant: TOSHIBA MEDICAL SYSTEMS CORPORATION, Otawara-shi (JP)

(72) Inventors: Yoshitomo Sakakura, Tochigi (JP); Kazuto Nogami, Tochigi (JP); Hidekazu Tanaka, Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 779 days.

(21) Appl. No.: 14/836,210

(22) Filed: Aug. 26, 2015

(65) Prior Publication Data

US 2015/0362570 A1    Dec. 17, 2015

Related U.S. Application Data

(63) Continuation of application No. PCT/JP2014/054969, filed on Feb. 27, 2014.

(30) Foreign Application Priority Data

Feb. 27, 2013  (JP) .................. 2013-037379

(51) Int. Cl.
*G01R 33/421*    (2006.01)
*G01R 33/385*    (2006.01)
(Continued)

(52) U.S. Cl.
CPC .......... *G01R 33/4215* (2013.01); *A61B 5/055* (2013.01); *G01R 33/385* (2013.01); *G01R 33/3873* (2013.01)

(58) Field of Classification Search
CPC .............. G01R 33/3873; G01R 33/385; G01R 33/4215; A61B 5/055
(Continued)

(56) References Cited

U.S. PATENT DOCUMENTS 4,990,877 A * 2/1991 Benesch ............ G01R 33/3873
324/318
5,635,839 A * 6/1997 Srivastava ......... G01R 33/3873
324/318
(Continued)

FOREIGN PATENT DOCUMENTS

CN    101334455 A    12/2008
CN    101957438 A    1/2011
(Continued)

OTHER PUBLICATIONS

Chinese office action dated May 16, 2017, in Patent Application No. CN 201480007076.5.
(Continued)

*Primary Examiner* — Rishi R Patel
(74) *Attorney, Agent, or Firm* — Nixon & Vanderhye P.C.

(57) ABSTRACT

A magnetic resonance imaging apparatus according to an embodiment includes a static field magnet, a gradient coil and a shim housing box. The static field magnet generates a static magnetic field in a space within a substantially cylindrical hollow. The gradient coil is provided inside the static field magnet and generates a gradient magnetic field. The shim housing box is capable of housing a metallic shim, the shim housing box being formed into a shape such that an attractive force of the static magnetic field applied to the shim housing box under magnetic excitation becomes smaller than a predetermined threshold.

12 Claims, 11 Drawing Sheets

(51) Int. Cl.
  *A61B 5/055* (2006.01)
  *G01R 33/3873* (2006.01)
(58) Field of Classification Search
  USPC .................................................. 324/318–320
  See application file for complete search history.

(56) References Cited

U.S. PATENT DOCUMENTS

| | | | |
|---|---|---|---|
| 5,786,695 A * | 7/1998 | Amor ................. | G01R 33/3873 324/319 |
| 2003/0222650 A1* | 12/2003 | Boemmel .......... | G01R 33/3873 324/322 |
| 2008/0191698 A1 | 8/2008 | Nogami | |
| 2008/0290871 A1 | 11/2008 | Tamura | |
| 2010/0237867 A1* | 9/2010 | Slade ................. | G01R 33/3873 324/314 |
| 2010/0271028 A1* | 10/2010 | Kawamoto ........ | G01R 33/3873 324/318 |
| 2011/0006769 A1 | 1/2011 | Iwasa et al. | |
| 2014/0009152 A1 | 1/2014 | Sakakibara | |
| 2014/0061202 A1* | 3/2014 | Mathieu ............. | G01R 33/3804 220/560.09 |

FOREIGN PATENT DOCUMENTS

| | | |
|---|---|---|
| JP | 2008-289703 | 12/2008 |
| JP | 2012-115474 | 6/2012 |
| WO | WO 2012/132911 | 10/2012 |

OTHER PUBLICATIONS

International Search Report for PCT/JP2014/054969, dated Mar. 25, 2014, 4 pages.
Written Opinion of the ISA for PCT/JP2014/054969, dated Mar. 25, 2014, 3 pages.

* cited by examiner

MAGNETIC RESONANCE IMAGING APPARATUS AND GRADIENT COIL

CROSS-REFERENCE TO RELATED APPLICATIONS

This application is a continuation of PCT international application Ser. No. PCT/JP2014/054969 filed on Feb. 27, 2014 which designates the United States, incorporated herein by reference, and which claims the benefit of priority from Japanese Patent Application No. 2013-037379, filed on Feb. 27, 2013, the entire contents of which are incorporated herein by reference.

FIELD

Embodiments described herein relate generally to a magnetic resonance imaging apparatus and a gradient coil.

BACKGROUND

Magnetic resonance imaging is an imaging technique in which the atomic nuclear spin of the subject placed in the static magnetic field is magnetically excited by using radio frequency (RF) pulses at the Larmor frequency, thereby generating images by using magnetic resonance signals data generated due to the excitation.

Uniformity of the static magnetic field is a prerequisite for the magnetic resonance imaging. Therefore shimming is conducted to correct the non-uniformity of the static magnetic field. Shimming is roughly classified into technique called passive shimming and technique called active shimming, or the like. Conventionally, the passive shimming is conducted by using an elongated tray-type shim housing box called a shim tray, or the like. Specifically, the shim tray includes multiple pockets along a longitudinal direction, and each pocket houses iron shims as appropriate. Then, the shim tray is inserted into a gantry device along the long axis direction of the cylindrical hollow.

During the insertion operation, the attractive force of the static magnetic field applied to the shim tray is about 50 kgw (kilogram-weight) at a maximum. Therefore, conventionally, during an operation to insert the shim tray into the gantry device, the static magnetic field is demagnetized each time; however, demagnetization is time-consuming, and also leads to helium gas consumption. Thus, the operation efficiency is decreased.

DETAILED DESCRIPTION

A magnetic resonance imaging apparatus according to an embodiment includes a static field magnet, a gradient coil and a shim housing box. The static field magnet generates a static magnetic field in a space within a substantially cylindrical hollow. The gradient coil is provided inside the static field magnet and generates a gradient magnetic field. The shim housing box is capable of housing a metallic shim, the shim housing box being formed into a shape such that an attractive force of the static magnetic field applied to the shim housing box under magnetic excitation becomes smaller than a predetermined threshold.

With reference to the drawings, an explanation is given below of a magnetic resonance imaging apparatus and a gradient coil according to an embodiment. It is noted that embodiments are not limited to the following embodiments. Moreover, in principle, the details that are explained according to each of the embodiments can be also applied to other embodiments.

First Embodiment

Figure 1:
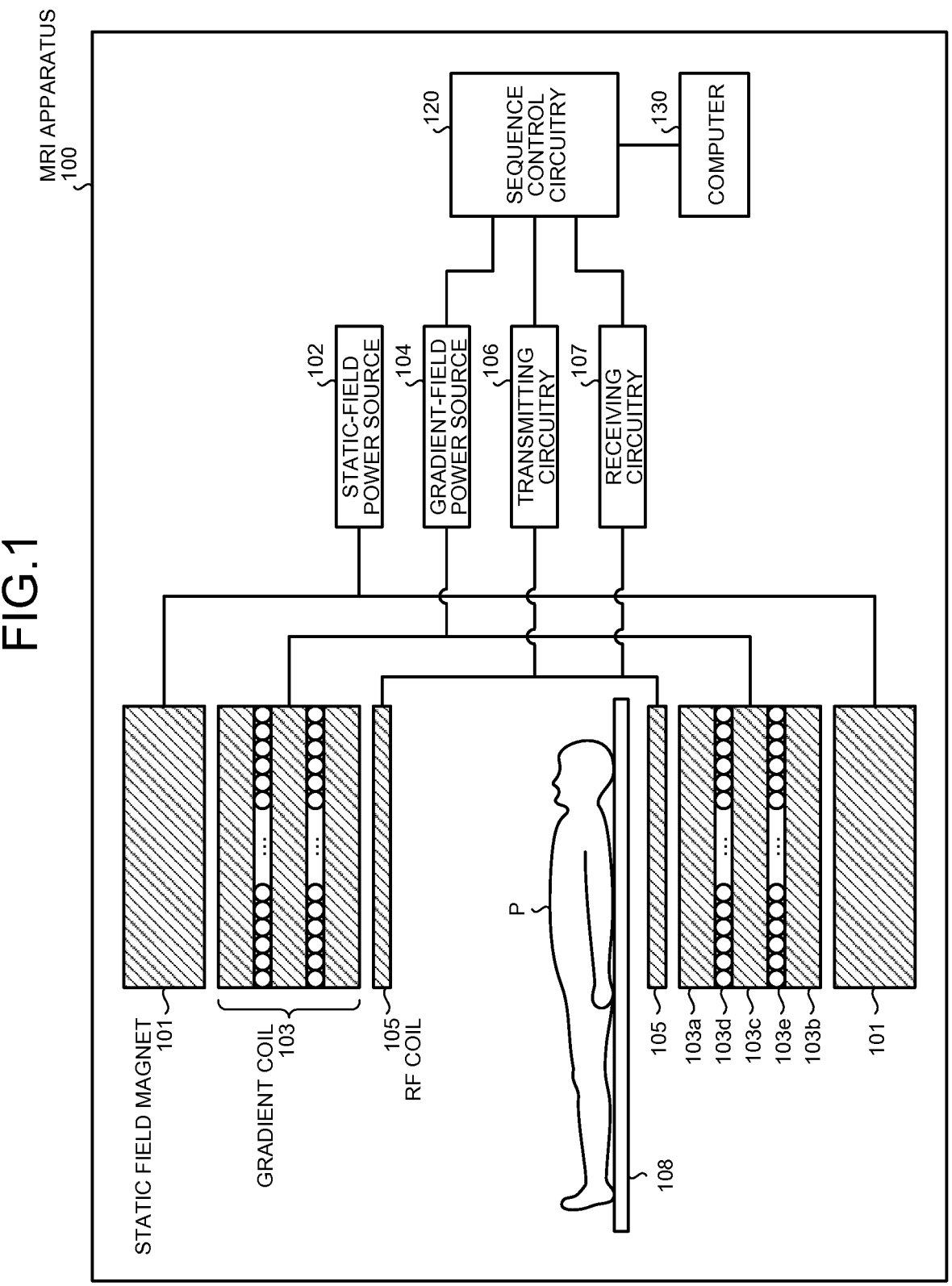
FIG. 1 is a block diagram that illustrates a configuration of an MRI apparatus according to a first embodiment.

FIG. 1 is a block diagram that illustrates a configuration of an MRI apparatus 100 according to a first embodiment. As illustrated in FIG. 1, the MRI apparatus 100 includes a static field magnet 101, a static-field power source 102, a gradient coil 103, a gradient-field power source 104, an RF coil 105, a transmitting circuitry 106, a receiving circuitry 107, a bed 108, a sequence control circuitry 120, and a computer 130. Here, the MRI apparatus 100 does not include a subject P (for example, a human body). Furthermore, the configuration illustrated in FIG. 1 is only an example. Each component/circuitry may be configured to be integrated or separated as appropriate.

The static field magnet 101 is a magnet that is formed into a cylindrical hollow shape, and it generates a static magnetic field in a space within a substantially cylindrical (including ellipsoidal) hollow. The static field magnet 101 is, for example, a superconducting magnet, and it is magnetically excited by receiving currents that are supplied by the static-field power source 102. The static-field power source 102 supplies currents to the static field magnet 101. Furthermore, the static field magnet 101 may be a permanent magnet and, in such a case, the MRI apparatus 100 may not include the static-field power source 102. Moreover, the static-field power source 102 may be provided separately from the MRI apparatus 100.

The gradient coil 103 is provided inside the static field magnet 101, and it is a coil that is formed into a hollow and substantially cylindrical shape. The gradient coil 103 receives currents that are supplied by the gradient-field power source 104 so as to generate a gradient magnetic field.

Furthermore, the gradient coil 103 is explained later in detail. The gradient-field power source 104 supplies currents to the gradient coil 103.

The RF coil 105 is located inside the gradient coil 103, and it receives RF pulses that are supplied by the transmitting circuitry 106 so as to generate a high-frequency magnetic field. Furthermore, the RF coil 105 receives magnetic resonance signals that are generated from the subject P due to the effect of the high-frequency magnetic field and outputs the received MR signals to the receiving circuitry 107.

Furthermore, the above-described RF coil 105 is only an example. The RF coil 105 may be configured by using any one or a combination of a coil that has only a transmitting function, a coil that has only a receiving function, and a coil that has a transmitting and receiving function.

The transmitting circuitry 106 supplies, to the RF coil 105, RF pulses that correspond to the Larmor frequency that is defined according to the type of target atom and the magnetic field intensity. The receiving circuitry 107 detects an MR signal that is output from the RF coil 105 and generates MR data on the basis of the detected MR signal. Specifically, the receiving circuitry 107 performs a digital conversion on the MR signal that is output from the RF coil 105 so as to generate MR data. Furthermore, the receiving circuitry 107 sends the generated MR data to the sequence control circuitry 120. Here, the receiving circuitry 107 may be provided on the side of the gantry device that includes the static field magnet 101, the gradient coil 103, or the like.

The bed 108 includes a top board on which the subject P is placed. For the convenience of explanation, FIG. 1 illustrates only the top board. Typically, the bed 108 is installed such that its longitudinal direction is parallel to the central axis of the cylindrical hollow of the static field magnet 101. Furthermore, the top board is movable in the longitudinal direction and in the vertical direction, and it is inserted into the space within the substantially cylindrical hollow inside the RF coil 105 in a state where the subject P is placed on the top board. Here, the space within the substantially cylindrical hollow is sometimes referred to as a "bore", or the like.

The sequence control circuitry 120 drives the gradient-field power source 104, the transmitting circuitry 106, and the receiving circuitry 107 on the basis of sequence information that is transmitted from the computer 130, thereby capturing an image of the subject P. Here, the sequence information is the information that defines the procedure for capturing. The sequence information defines the intensity of currents that are supplied by the gradient-field power source 104 to the gradient coil 103, the timing for supplying currents, the intensity of RF pulses that are supplied by the transmitting circuitry 106 to the RF coil 105, the timing for applying RF pulses, the timing for detecting MR signals by the receiving circuitry 107, or the like.

For example, the sequence control circuitry 120 is an integrated circuit, such as an application specific integrated circuit (ASIC) or a Field Programmable Gate Array (FPGA), or an electronic circuit, such as a central processing unit (CPU) or a micro processing unit (MPU).

Furthermore, as a result of capturing of the subject P by driving the gradient-field power source 104, the transmitting circuitry 106, and the receiving circuitry 107, the sequence control circuitry 120 receives MR data from the receiving circuitry 107 and transmits the received MR data to the computer 130.

The computer 130 performs overall control on the MRI apparatus 100. Furthermore, the computer 130 performs reconstruction processing, such as Fourier transform, on the MR data that is transferred from the sequence control circuitry 120, thereby generating an MR image, or the like. For example, the computer 130 includes control circuitry, storage, an input unit, and a display. The control circuitry is an integrated circuit, such as an ASIC or FPGA, or an electronic circuit, such as a CPU or MPU. The storage is a semiconductor memory device, such as a random access memory (RAM) or a flash memory, a hard disk, an optical disc, or the like. The input unit is a pointing device, such as a mouse or trackball, a selecting device, such as a mode changeover switch, or an input device, such as a keyboard. The display is a display device, such as a liquid crystal display device.

Figure 2:
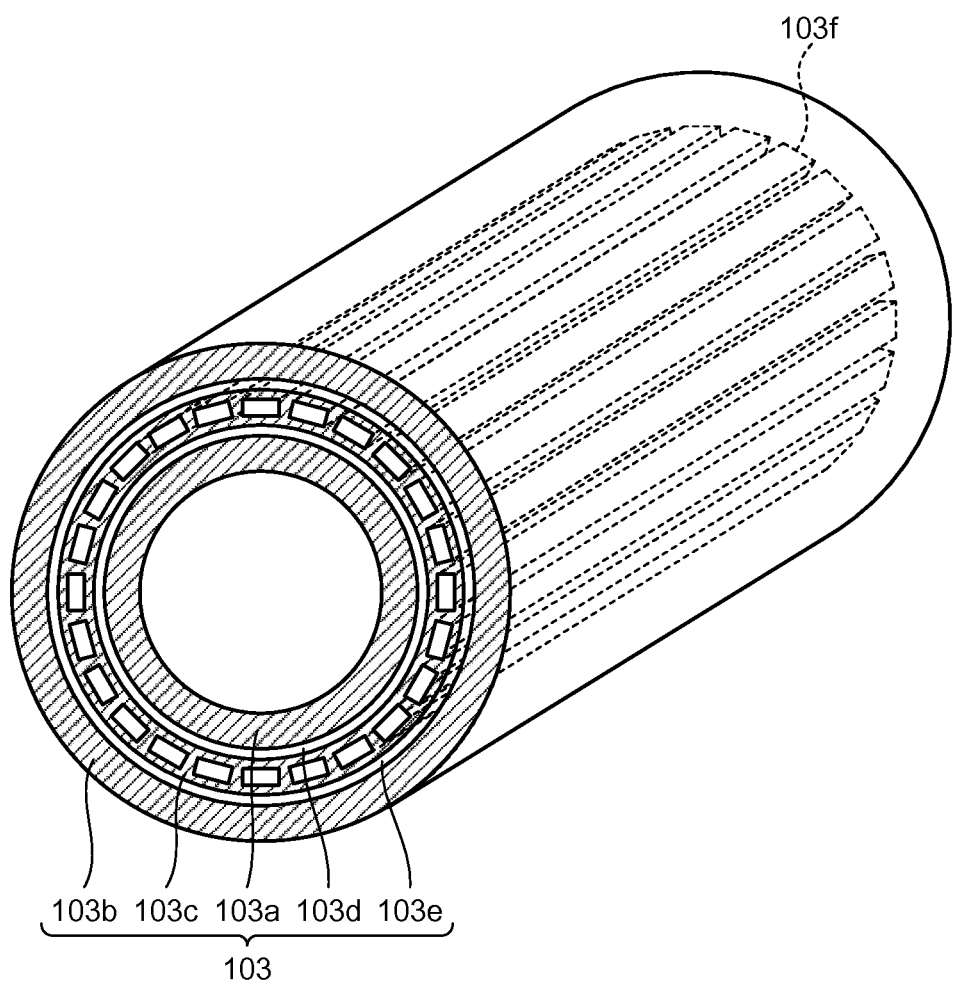
FIG. 2 is a perspective view that illustrates a structure of a gradient coil according to the first embodiment.

FIG. 2 is a perspective view that illustrates a structure of the gradient coil 103 according to the first embodiment. Here, according to the first embodiment, the gradient coil 103 is an actively shielded gradient coil (ASGC), and it includes a main coil 103a that generates a gradient magnetic field and a shield coil 103b that generates the magnetic field that is designed for shielding and that cancels out leaked magnetic fields. As illustrated in FIG. 2, the main coil 103a, a cooling layer 103d in which a cooling tube is provided, a shim layer 103c in which an iron shim is provided, a cooling layer 103e in which a cooling tube is provided, and the shield coil 103b are laminated in the gradient coil 103 in order, starting from the inner side that is closest to the space within the substantially cylindrical hollow.

Multiple (e.g., 24) shim-pocket insertion guides 103f are formed in the shim layer 103c. As illustrated in FIG. 2, the shim-pocket insertion guides 103f are typically the holes penetrating through the entire length of the gradient coil 103 in a long axis direction, and they are formed at equal intervals in a circumferential direction. Furthermore, insertion openings of the shim-pocket insertion guides 103f are provided at multiple locations on the edge surface (the shim layer 103c) of the gradient coil 103. Multiple (e.g., 15) shim pockets (not illustrated in FIG. 2) are arranged side by side in the long axis direction within the shim-pocket insertion guide 103f. The shim pockets are explained in detail later.

Typically, cooling tubes are arranged in the cooling layer 103d and the cooling layer 103e in a helical fashion in conformity with the substantially cylindrical shape (not illustrated in FIG. 2). Although not illustrated in FIG. 1, the MRI apparatus 100 according to the first embodiment further includes a cooling device that includes a heat exchanger or a circulating pump, and the cooling device circulates a cooling medium, such as water, through the cooling tube, thereby cooling the gradient coil 103. Thus, the cooling systems of the MRI apparatus 100 are provided in intermediate layers of the gradient coil 103 such that they sandwich iron shims.

Figure 3:
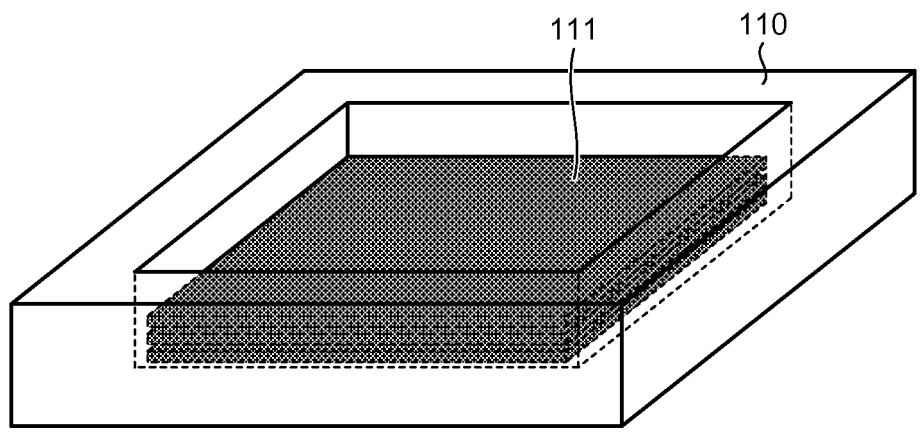
FIG. 3 is a diagram that illustrates a shim pocket according to the first embodiment.
Figure 4:
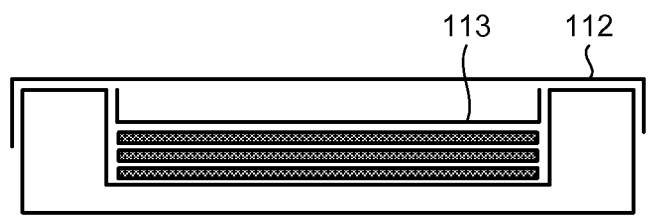
FIG. 4 is a diagram that illustrates the shim pocket according to the first embodiment.

FIG. 3 and FIG. 4 are diagrams that illustrate a shim pocket 110 according to the first embodiment. According to the first embodiment, an iron shim 111 is housed in the shim pocket 110 as illustrated in FIG. 3 instead of being housed in a tray-type shim tray that has a plurality of pockets along a longitudinal direction. As illustrated in FIG. 3, the shim pocket 110 is a box-type housing box capable of laminating and housing the iron shims 111. Furthermore, FIG. 3 illustrates a state where three iron shims are housed. Moreover, the shim pocket 110 illustrated in FIG. 3 and FIG. 4 is only an example, and the configuration may be changed as appropriate as long as it is a relatively small housing box capable of housing an iron shim.

The box-type shim pocket 110 is formed to have a size such that, when the static field magnet is under magnetic excitation and while the iron shims 111 are laminated, the attractive force of the static magnetic field applied to the shim pocket 110 becomes smaller than a predetermined threshold. Typically, the shim pocket 110 may be formed to have a size corresponding to a conventional shim tray that is divided in units of pockets. Furthermore, there is no limitation on the size of the shim pocket 110. As described later, it may have a size such that it is possible to perform an operation to insert it into the shim-pocket insertion guide 103f when the static field magnet is magnetically excited, and the threshold for the attractive force for determining the size may be defined as appropriate when the shim pocket is designed, or the like.

FIG. 4 is a cross-sectional view of the shim pocket 110, and it illustrates a state where a cover 112 is placed over the shim pocket 110. There is a possibility that, when magnetically excited by the static field magnet, the iron shim 111 slips through the clearance of the shim pocket 110 due to the attractive force of the static magnetic field. Therefore, it is preferable to place a cover over the shim pocket 110 by using any technique. Furthermore, as illustrated in FIG. 4, there is a possibility that, if the small number of the iron shims 111 is housed in the shim pocket 110, the iron shim 111 moves during the imaging, which causes noises. Therefore, for example, it is preferable that the shim pocket 110 is provided with a mechanism 113 for pressing the iron shim as illustrated in FIG. 4.

Furthermore, an operator inserts the individual shim pocket, in which an iron shim is housed as appropriate, into the shim-pocket insertion guide 103f 110 one by one. As described above, the shim pocket 110 is formed to have a size such that the attractive force of the static magnetic field that is applied to the shim pocket 110 is smaller than a predetermined threshold. Therefore, when magnetically excited by the static field magnet, an attractive force generated in the individual shim pocket 110 is not large. Therefore, it is not necessary to demagnetize the static magnetic field each time an operation is performed to insert the shim pocket 110 into the shim-pocket insertion guide 103f. In other words, it is possible to continuously perform an operation to insert the shim pocket 110 when the static field magnet is magnetically excited.

Figure 5:
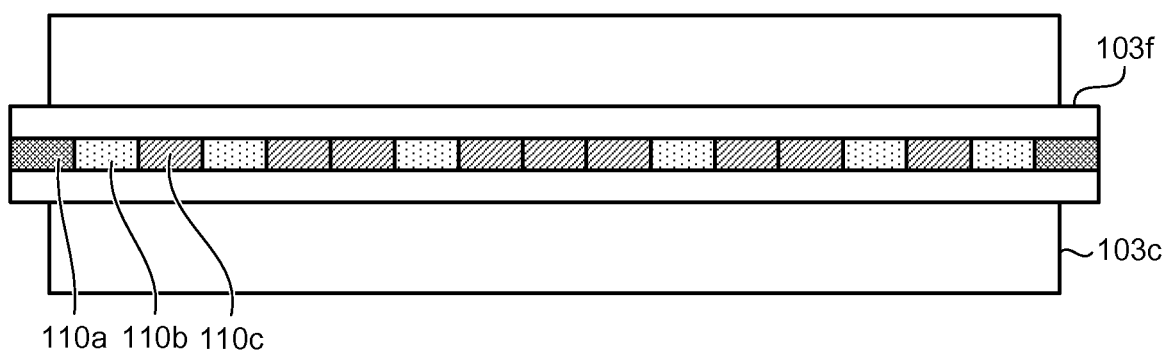
FIG. 5 is a diagram that illustrates the shim pocket that is inserted into the gradient coil according to the first embodiment.

FIG. 5 is a diagram that illustrates the shim pocket 110 that is inserted into the gradient coil 103 according to the first embodiment. FIG. 5 is a cross-sectional view of the shim layer 103c of the gradient coil 103, and it illustrates a state where the shim pockets 110 are sequentially inserted into the shim-pocket insertion guide 103f penetrating through the entire length in a long axis direction. Furthermore, in FIG. 5, for the convenience of explanation, discrimination is made by using three patterns. A pattern 110a does not indicate the shim pocket 110 but indicates a cover that is located on both ends of the shim-pocket insertion guide 103f instead of the shim pocket 110. A pattern 110b indicates the vacant shim pocket 110 in which an iron shim is not housed. A pattern 110c indicates the shim pocket 110 in which an iron shim is housed.

According to the first embodiment, for example, the 15 shim pockets 110 are sequentially inserted into the shim-pocket insertion guide 103f. Furthermore, the covers are located on both ends. For example, an operator inserts the shim pocket 110 one by one through one of the insertion openings that are formed on both ends of the shim-pocket insertion guide 103f. In this case, a cover may be placed in advance on the insertion opening that is on the opposite side of the insertion opening through which the shim pocket 110 is inserted. Furthermore, the operator sequentially pushes the previously inserted shim pocket 110 forward by using the subsequent shim pocket 110, thereby finishing inserting all of the 15 shim pockets 110. Then, finally, the cover is placed on the insertion opening through which the shim pockets 110 are inserted.

Furthermore, according to the first embodiment, for example, the operator may insert the shim pocket 110 through at least either of two insertion openings formed on both ends of the shim-pocket insertion guide 103f.

FIG. 6A, FIG. 6B, FIG. 7A, FIG. 7B, and FIG. 7C are diagrams that illustrate the cover of the shim-pocket insertion guide 103f according to the first embodiment. The operator needs to place the cover on the two insertion openings, which are formed on both ends of the shim-pocket insertion guide 103f, by using any method. Here, as described above, according to the first embodiment, the operator can insert the shim pocket 110 through both of the two insertion openings that are formed on both ends of the shim-pocket insertion guide 103f; therefore, it is preferable that the cover, which is placed on the two ends, is formed with a mechanism operable to easily detach instead of being secured by using an adhesive agent, or the like.

Figure 6A:
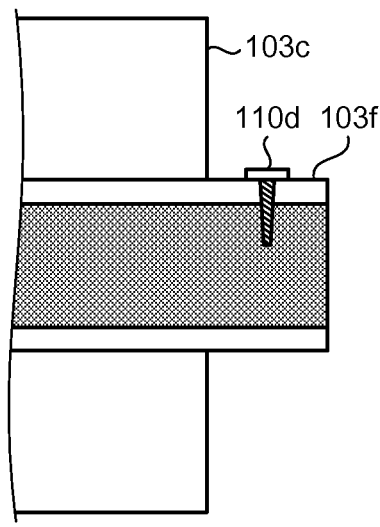
FIG. 6A, FIG. 6B, FIG. 7A, FIG. 7B and FIG. 7C are diagrams that illustrate a cover of a shim-pocket insertion guide according to the first embodiment.
Figure 6B:
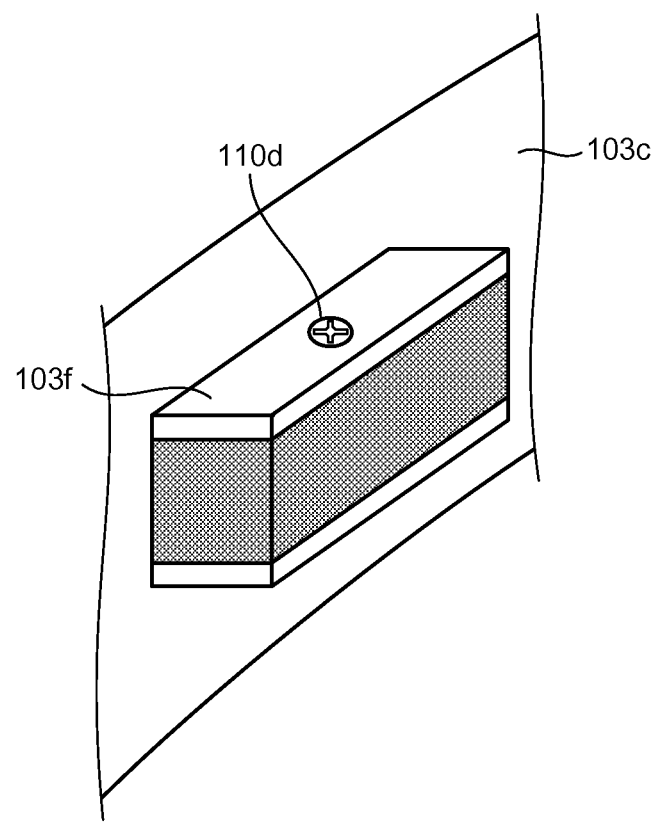

For example, as illustrated in FIG. 6A and FIG. 6B, the cover of the shim-pocket insertion guide 103f may be formed by using a simple screw fastening mechanism. FIG. 6A and FIG. 6B are diagrams that illustrate the right end section of the shim-pocket insertion guide 103f, which is illustrated in FIG. 5, in an enlarged manner, FIG. 6A is a cross-sectional view, and FIG. 6B is a perspective view.

Figure 7A:
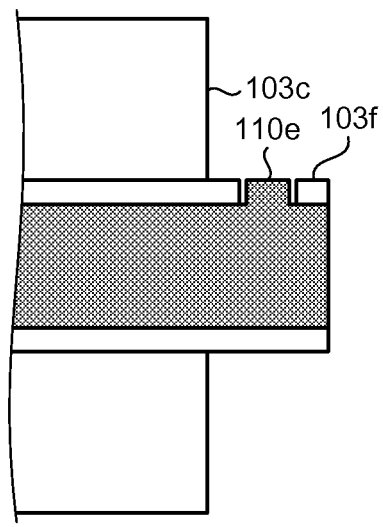
Figure 7B:
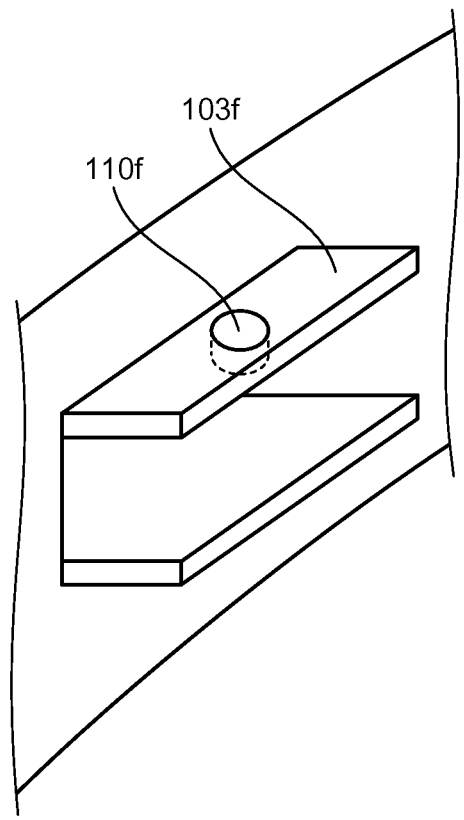
Figure 7C:
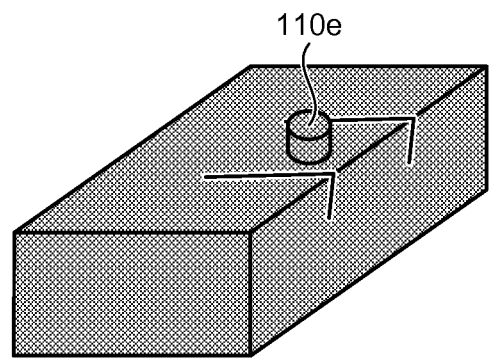

Furthermore, for example, the mechanism illustrated in FIG. 7A to FIG. 7C may be appropriate. Similarly, FIG. 7A to FIG. 7C are diagrams that illustrate the right end section of the shim-pocket insertion guide 103f, which is illustrated in FIG. 5, in an enlarged manner, FIG. 7A is a cross-sectional view, FIG. 7B is a perspective view (however, the cover is not inserted), and FIG. 7C illustrates the cover itself. As illustrated in FIG. 7A to FIG. 7C, for example, the mechanism may be such that a hole 110f is formed on the side of the shim-pocket insertion guide 103f, a convex section 110e is formed on the cover and, when the cover is inserted into the shim-pocket insertion guide 103f, the convex section 110e is interdigitated to the hole 110f. In this case, for example, a configuration is such that the cover is provided with cuts that are illustrated in FIG. 7C so that the part that includes the convex section 110e can be pushed downward. The mechanism is such that, when the cover is inserted into the shim-pocket insertion guide 103f, the part that includes the convex section 110e is pushed downward due to the cuts and, when the convex section 110e reaches the hole 110f that is formed on the side of the shim-pocket insertion guide 103f, it is interdigitated to the hole 110f and then the part that includes the convex section 110e is returned upward.

Furthermore, the structure of the cover that is illustrated with reference to FIG. 6A, FIG. 6B, FIG. 7A, FIG. 7B, and FIG. 7C is only an example, and it may be changed as appropriate. Furthermore, a mechanism operable to easily detach may be formed on the shim pocket 110 itself so that both ends or one end of the shim-pocket insertion guide 103f is covered by the shim pocket 110 itself. Furthermore, for example, in an environment where the shim pocket 110 is inserted through only one of the insertion openings that are formed on both ends of the shim-pocket insertion guide 103f, or the like, the cover of the shim-pocket insertion guide 103f may be secured by using an adhesive agent, or the like.

Figure 8:
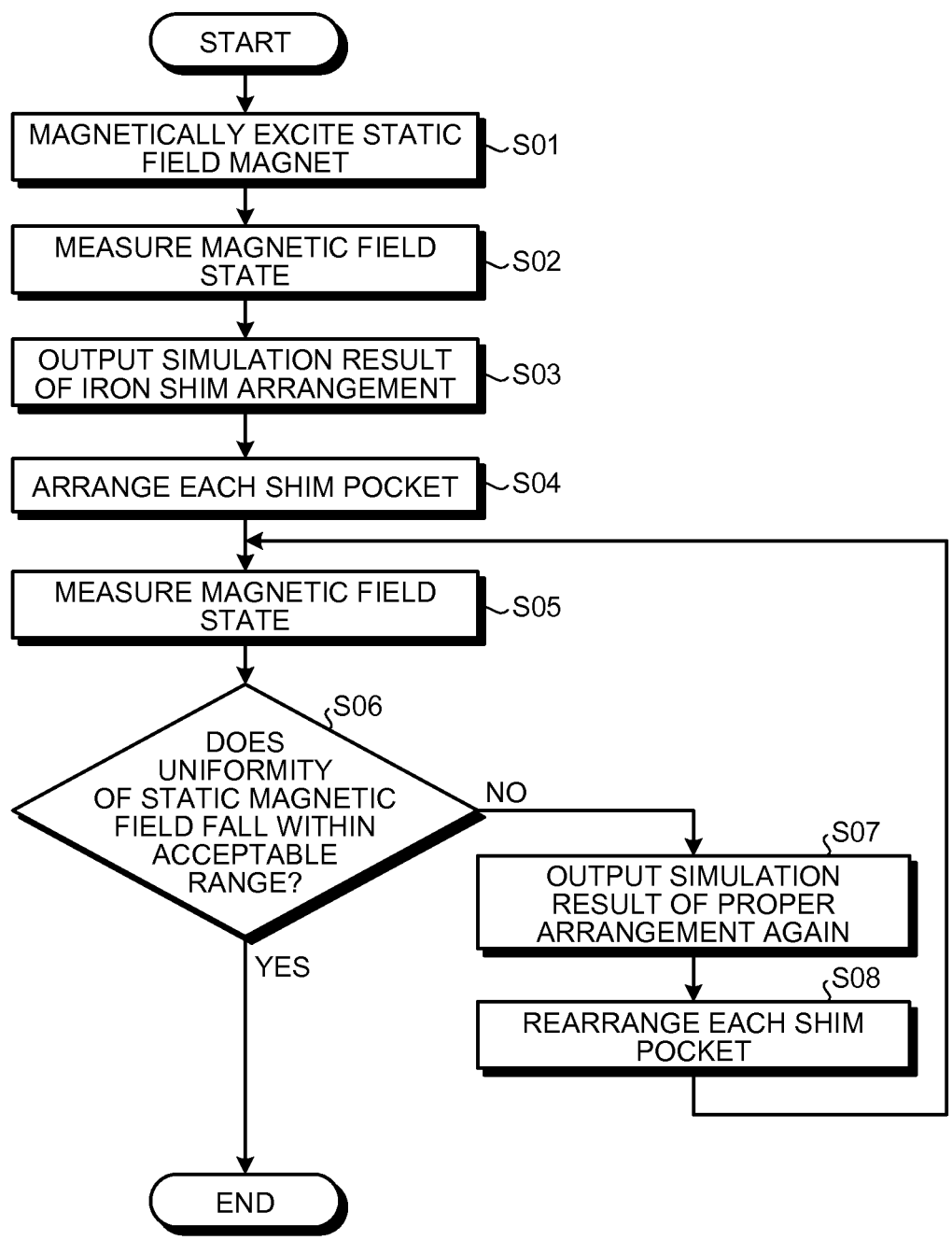
FIG. 8 is a diagram that illustrates the operation flow of shimming according to the first embodiment.

FIG. 8 is a diagram that illustrates the operation flow of shimming according to the first embodiment. FIG. 8 illustrates the flow of an operation to insert the shim pocket 110 into the shim-pocket insertion guide 103f that is formed on the gradient coil 103. This operation is usually performed when the MRI apparatus 100 is installed, or the like.

As illustrated in FIG. 8, the static-field power source 102 first supplies currents so that the static field magnet 101 is magnetically excited (Step S01). Next, the operator measures the state of the magnetic field by using a measurement device that is called a field camera, or the like (Step S02).

After the measurement result is input to the computer 130, the computer that is brought by the operator, or the like, the computer outputs a simulation result related to the arrangement of iron shims (Step S03). For example, the computer outputs a simulation result that indicates "out of the 24 formed shim-pocket insertion guides 103f, please insert some number of iron shims of some kind into the shim pocket 110 that is located at some position of the some-number-th shim-pocket insertion guide 103f".

Then, the operator arranges each of the shim pockets 110 in accordance with the simulation result (Step S04). Specifically, the operator houses the designated number of iron shims in the shim pocket 110 and inserts the shim pocket 110, which houses the iron shims, in the designated shim-pocket insertion guide 103f in the designated order.

After the operator completes the operation to insert, for example, the 15 shim pockets 110 in the 24 lines, the operator again measures the magnetic field state (Step S05). After the measurement result is input to the computer, or the like, the computer determines whether the uniformity of the static magnetic field falls within a predetermined acceptable range (Step S06). Then, if it falls within the acceptable range (Step S06, Yes), the operation to insert the shim pocket 110 is thus completed.

Conversely, if it does not fall within the acceptable range (Step S06, No), the computer again outputs a simulation result related to the proper arrangement of iron shims (Step S07); therefore, the operator rearranges each of the shim pockets 110 in accordance with the simulation result that is output again (Step S08). Furthermore, in general, the rearrangement is often performed by, instead of remaking the entire arrangement, remaking the arrangement of some of the shim pockets 110 as a fine adjustment for achieving the proper state of uniformity of the static magnetic field.

Thus, the operations from Step S05 to Step S08 are repeated as appropriate, about 4 to 5 times at most, so that the uniformity of the static magnetic field falls within the acceptable range at last, and the operation to insert the shim pocket 110 is completed.

As described above, according to the first embodiment, the shim housing box, which is handled by the operator, is not an elongated tray-type shim tray but the box-type shim pocket 110 and, when the static field magnet 101 is magnetically excited, a small attractive force of the static magnetic field is applied to the shim pocket 110. Therefore, operators can perform an insertion operation without demagnetizing the static magnetic field, which is conventionally performed by repeating excitation and demagnetization of the static magnetic field, and thus the efficiency of a shimming operation can be improved.

Second Embodiment

Figure 9A:
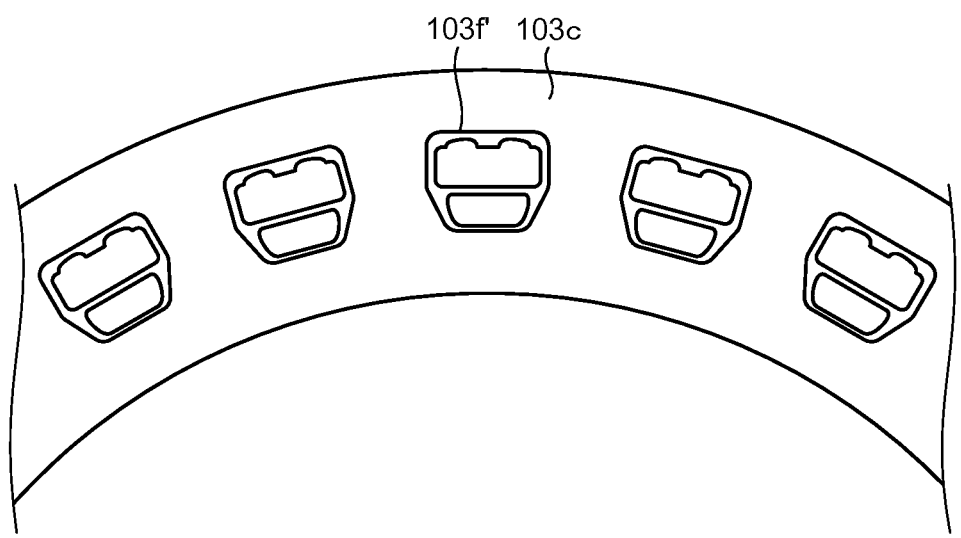
FIG. 9A and FIG. 9B are diagrams that illustrate a shim-pocket insertion guide according to a second embodiment.
Figure 9B:
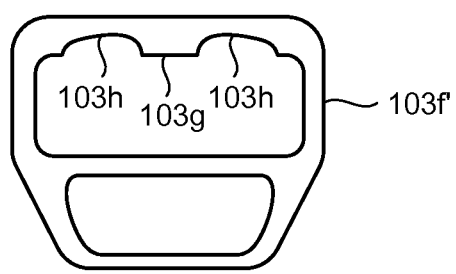

Next, a second embodiment is explained. FIG. 9A and FIG. 9B are diagrams that illustrate a shim-pocket insertion guide 103f according to the second embodiment. As illustrated in FIG. 9A and FIG. 9B, according to the second embodiment, the shim-pocket insertion guide 103f is formed such that it is separated into multiple tiers, i.e., two tiers that are the upper and lower tiers. FIG. 9A is a diagram of the shim layer 103c of the gradient coil 103 when it is viewed from the front side, and FIG. 9B is a diagram of the shim-pocket insertion guide 103f when it is viewed from the front side. As illustrated in FIG. 9B, the shim-pocket insertion guide 103f is formed such that it is separated into a first tier that is relatively large and a second tier that is smaller compared to the first tier.

Here, for example, like the first tier that is illustrated in FIG. 9B, the shim-pocket insertion guide 103f is inclusive of concave portions 103h and a convex portion 103g on its inner wall side. The concave portion 103h and the convex portion 103g are typically formed through substantially the entire length in a long axis direction; however, there is no limitation on the embodiment, and it may be formed such that it is scattered in a long axis direction. If the concave portion 103h and the convex portion 103g are formed on the inner wall of the shim-pocket insertion guide 103f as described above, for example, the shim pocket 110 is inserted into the shim-pocket insertion guide 103f such that the part of the cover 112 is in contact with the convex portion 103g. In this case, the oscillation of the shim pocket 110 within the shim-pocket insertion guide 103f can be reduced and, as the air layer that is formed between the concave portion 103h and the shim pocket 110 serves as an adiabatic layer, changes in the temperature of the iron shim 111 can be suppressed. The concave portion 103h and the convex portion 103g illustrated in FIG. 9B are only examples. For example, the convex portions 103g may be provided at two or more locations in a circumferential direction, and the corresponding number of the concave portions 103h may be provided.

Figure 10:
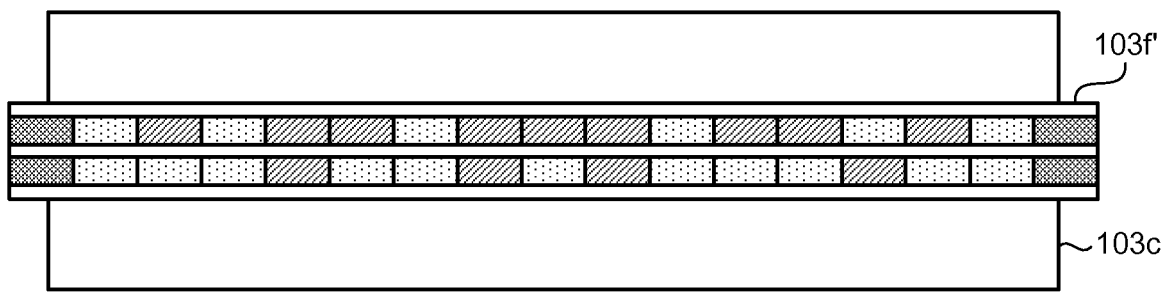
FIG. 10 is a diagram that illustrates the shim pocket that is inserted into the gradient coil according to the second embodiment.

FIG. 10 is a diagram that illustrates the shim pocket 110 that is inserted into the gradient coil 103 according to the second embodiment. FIG. 10 is a cross-sectional view of the shim layer 103c of the gradient coil 103, and it illustrates a state where the shim pockets 110 are sequentially inserted into the upper and lower tiers of the shim-pocket insertion guide 103f penetrating through the entire length in a long axis direction. Furthermore, the discrimination by using three patterns in FIG. 10 has the same meaning as the discrimination in FIG. 5. Moreover, in the illustration of FIG. 10, the sizes of the upper and lower tiers are the same; however, there is no limitation on the embodiment, and changes may be made as appropriate such that, for example, the size of the shim pocket 110 that is inserted into the second lower tier is smaller than that of the shim pocket 110 that is inserted into the first upper tier, and the number of them to be inserted is larger. Conversely, the size of the shim pocket 110 that is inserted into the second lower tier may be larger, and the number of them to be inserted may be smaller.

Specifically, the space into which the shim pockets 110 are inserted is first separated into multiple spaces as described above so that the number of the iron shims 111 that are housed in the single shim pocket 110 can be reduced and, as a result, the attractive force applied to the single shim pocket 110 can be further reduced.

Furthermore, for example, by delegating roles among the multiple tiers, such as main or sub, the efficiency of rearrangement can be further improved. Specifically, during the operation flow that is explained with reference to, for example, FIG. 8, a simulation result is output during the first simulation (Step S04) on the basis of the assumption that an arrangement is made for only the first tier that is a main, and a simulation result is output at the subsequent fine adjustment step (after Step S05) on the basis of the assumption that an arrangement is subsidiarily made to the second tier that is a sub. Thus, it is possible to make a fine adjustment without removing the temporarily inserted shim pocket 110, and it is considered that the operation efficiency can be further improved.

Furthermore, in the example that is illustrated according to the second embodiment, the size of each tier is different; however, there is no limitation on the embodiment and, for example, the sizes of the upper and lower tiers may be the same. Moreover, they may be separated into three or more tiers instead of the two tiers or may be separated into right and left tiers instead of the upper and lower tiers.

Other Embodiments

Embodiments are not limited to the above-described embodiments.

Figure 11:
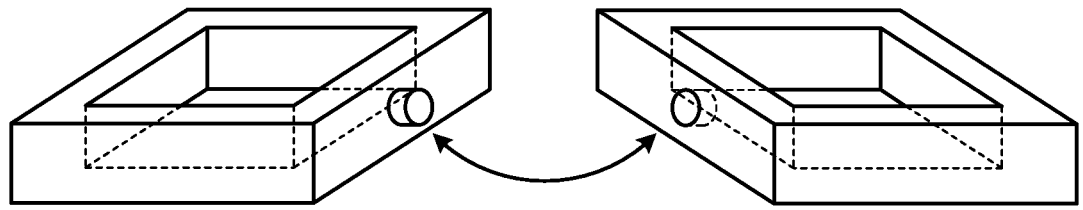
FIG. 11 is a diagram that illustrates connectable shim pockets according to other embodiments.

FIG. 11 is a diagram that illustrates connectable shim pockets according to a different embodiment. As explained in the above-described embodiment, a vacant shim pocket, in which no iron shim is housed, and a shim pocket, in which an iron shim is housed, are sometimes stored in combination in a shim-pocket insertion guide. Furthermore, for example, there may be a shim pocket in which the small number of iron shims is housed. Therefore, for example, as illustrated in FIG. 11, a shim pocket may be provided with a mechanism with which shim pockets can be easily connected. For example, as illustrated in FIG. 11, a shim pocket includes a convex portion and a concave portion on each of side surfaces, respectively and it is connectable to other adjacent shim pockets via the convex portion or the concave portion. Moreover, for the convenience of explanation, FIG. 11 illustrates only the convex portion or the concave portion; however, a shim pocket includes both of them, and it is connected to previous and next adjacent shim pockets.

Furthermore, if the above connection is made, also in the simulation result on the side of the computer, it is preferable to present the simulation result taking into the consideration of the attractive force applied to a group of connected shim pockets, that is, to what extent the shim pockets can be connected. An operator is capable of connecting the allowed group of shim pockets in accordance with the simulation result.

Figure 12:
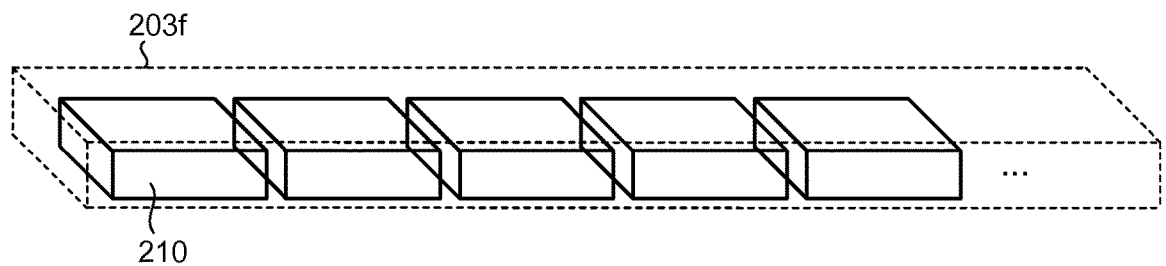
FIG. 12, FIG. 13 and FIG. 14 are diagrams that illustrate a shim housing box according to other embodiments.
Figure 13:
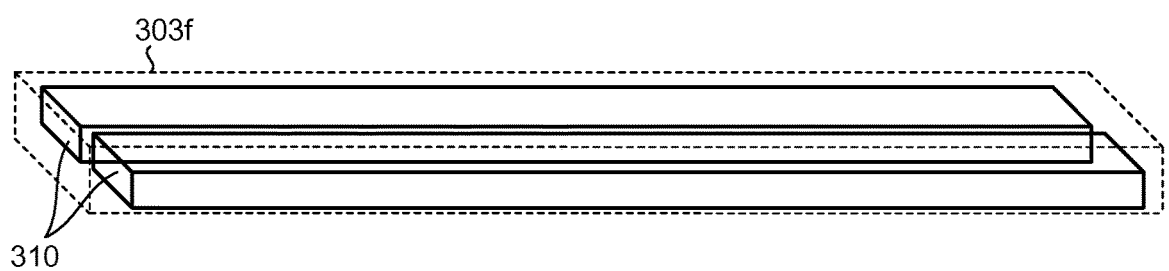
Figure 14:
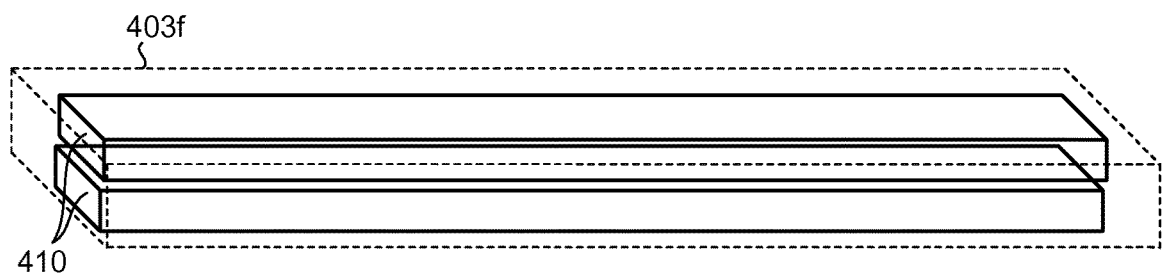

Next, FIG. 12 to FIG. 14 are diagrams that illustrate a shim housing box according to a different embodiment, and FIG. 15A, FIG. 15B, FIG. 16A, and FIG. 16B are diagrams that illustrate a shim insertion cavity according to a different embodiment. When taken together the above-described embodiments, in any case, the shim housing box (for example, the shim pocket 110) is formed into a shape to reduce the attractive force of the static magnetic field. Possible techniques for implementing the shape to reduce the attractive force of the static magnetic field that is applied to the shim housing box is roughly classified as the first technique for implementing a measure to the shim housing box itself, the second technique for implementing a measure to the shim insertion cavity itself into which the shim housing box is inserted, and the technique with the combination of the above. In the following, an explanation is given of the first technique and the second technique with reference to FIG. 12 to FIG. 16B.

First, the first technique is explained. As explained above, on an edge surface of the gradient coil 103, insertion openings of shim insertion cavities penetrating through an entire length in a long axis direction are provided at multiple locations. The shim housing box is designed to be inserted into one of the shim insertion cavities through one of the insertion openings. For example, as illustrated in FIG. 12, per one shim insertion cavity 203f, multiple shim housing boxes 210 are arranged side by side along the long axis direction of the substantially cylindrical hollow. This configuration corresponds to the typical shim pocket 110 that is explained in the first embodiment. Furthermore, FIG. 12 illustrates a case where the five or more shim housing boxes 210 are arranged side by side in a long axis direction; however, there is no limitation on the embodiment. The number of the shim housing boxes 210 that are arranged side by side in a long axis direction may be two, for example. That is, the number may be of any number. Furthermore, a plurality of the shim pockets 110 connected in advance, which are explained in the first embodiment, may be further arranged side by side in a long axis direction. Moreover, the shape of the shim insertion cavity 203f or the shim housing box 210 is not limited to the rectangle that is illustrated in FIG. 12 and, for example, the cylindrical shim housing box 210 may be inserted into the cylindrical shim insertion cavity 203f.

Furthermore, another example of the first technique is explained with reference to FIG. 13. For example, as illustrated in FIG. 13, per one shim insertion cavity 303f, shim housing boxes 310 are arranged side by side in multiple columns, in a circumferential direction of the substantially cylindrical hollow. For example, the shim-tray type shim housing box 310 that includes multiple pockets in a longitudinal direction is possible. As it is separated in a circumferential direction, the attractive force of the static magnetic field to the single shim housing box 310 is reduced.

Furthermore, another example of the first technique is explained with reference to FIG. 14. For example, as illustrated in FIG. 14, per one shim insertion cavity 403f, shim housing boxes 410 are arranged side by side in multiple columns, in a radial direction of the substantially cylindrical hollow. For example, the shim-tray type shim housing box 410 that includes multiple pockets in a longitudinal direction is possible. As it is separated in a radial direction, the attractive force of the static magnetic field that is applied to the single shim housing box 410 is reduced.

Furthermore, the techniques that are illustrated in FIG. 12, FIG. 13, and FIG. 14 may be combined as appropriate. For example, FIG. 12 illustrates the technique with which multiple shim housing boxes are arranged side by side in a long axis direction, and FIG. 13 illustrates the technique with which multiple shim housing boxes are arranged side by side in columns in a circumferential direction; however, they may be combined so that multiple shim housing boxes are arranged side by side in columns in a circumferential direction and are also arranged side by side in a long axis direction. In the same manner, multiple shim housing boxes may be arranged side by side in columns in a radial direction and also arranged side by side in a long axis direction. Alternatively, multiple shim housing boxes may be arranged side by side in columns in a circumferential direction and in a radial direction and also arranged side by side in a long axis direction. Multiple techniques are combined if necessary or the number of shim housing boxes arranged side by side is adjusted so that the configuration may be more suitable for a fine adjustment. In a case where an adjustment is made during maintenance while only one of the two insertion openings, which are formed on both ends in a long axis direction, is closed or opened, it typically can be said that the smaller the size of the single shim housing box that can be inserted through one of the insertion openings, the easier the fine adjustment is.

Next, the second technique is explained. As explained above, on an edge surface of the gradient coil 103, the insertion openings of the shim insertion cavities penetrating through the entire length in a long axis direction are provided at multiple locations, and the shim housing box is inserted into the shim insertion cavity through the insertion opening. Here, with the second technique, a group of insertion openings of the shim insertion cavities is provided at the locations scattered in a circumferential direction. This example corresponds to the shim-pocket insertion guide 103f' that is explained in the second embodiment and that is formed such that it is separated into multiple tiers. As an example, two tiers of the upper tier and the lower tier.

Figure 15A:
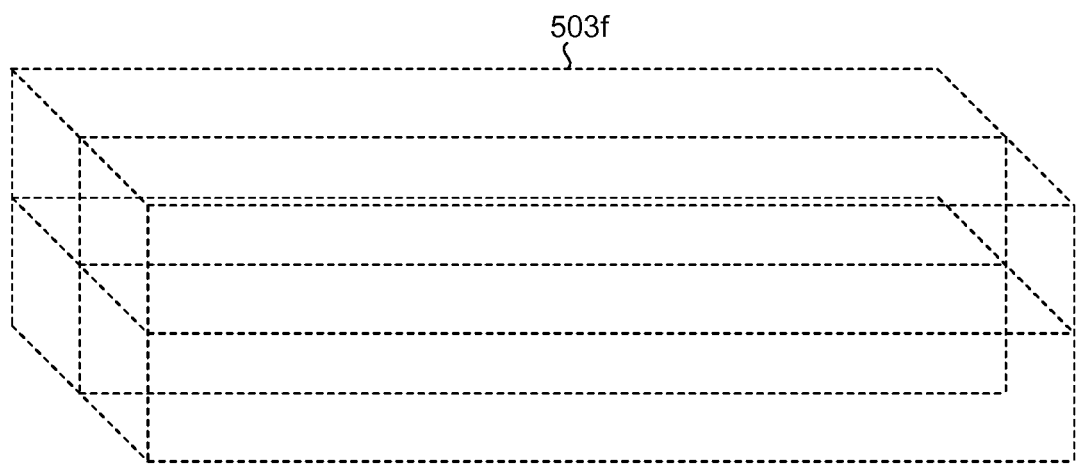
FIG. 15A, FIG. 15B, FIG. 16A and FIG. 16B are diagrams that illustrate a shim insertion cavity according to other embodiments.
Figure 15B:
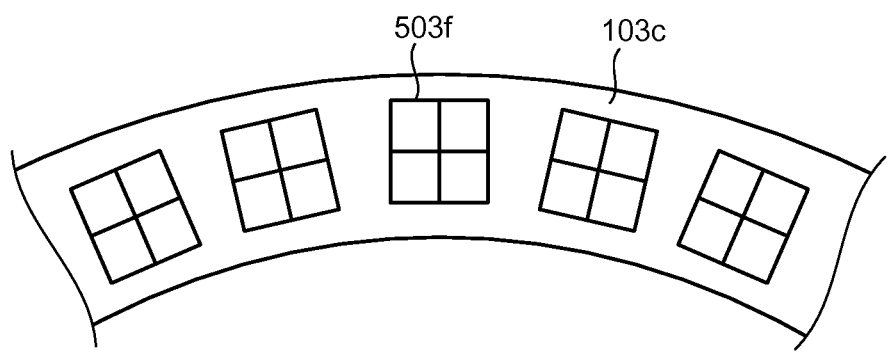

Here, an explanation is given by using another example. As illustrated in FIG. 15A, for example, a group shim insertion cavity 503f is formed by putting together four shim insertion cavities in total, i.e., two in a vertical direction and two in a horizontal direction. As illustrated in FIG. 15B, the group of insertion openings is provided at each of the locations scattered in a circumferential direction. As the size of a single shim insertion cavity is smaller, it is considered that the attractive force of the static magnetic field that is applied to the shim housing box 310, which is formed in accordance with the size of the shim insertion cavity, is reduced.

Furthermore, FIG. 15A and FIG. 15B illustrate a case where the four shim insertion cavities 503f are arranged in one piece; however, there is no limitation on the embodiment. The number of the shim insertion cavities 503f that are arranged in one piece may be of any number. Furthermore, the shape of the shim insertion cavity 203f is not limited to the rectangle that is illustrated in FIG. 15A and, for example, the cylindrical shim insertion cavity 503f may be appropriate.

Figure 16A:
Figure 16B:
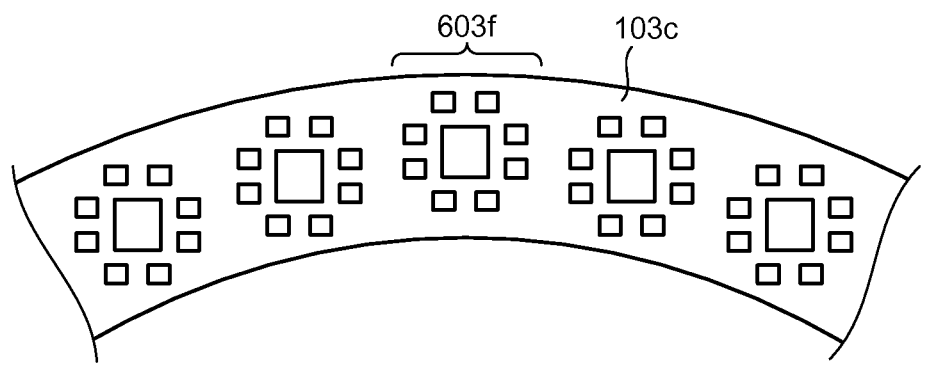

Furthermore, for example, as illustrated in FIG. 16A and FIG. 16B, a shim insertion cavity 603f may be configured such that the main shim insertion cavity 603f is surrounded by the sub shim insertion cavities 603f. In this case, too, there is no limitation on the embodiment. The roles, such as main or sub, may not be always divided, and the number of the shim insertion cavities 603f that are arranged in one piece is of any number. Moreover, the shape of the shim insertion cavity 603f is not limited to the rectangle that is illustrated in FIG. 16A and, for example, the cylindrical shim insertion cavity 603f may be appropriate.

Furthermore, the first technique and the second technique may be combined as appropriate. For example, multiple shim housing boxes may be arranged side by side in a long axis direction or may be arranged side by side in columns in a circumferential direction or in a radial direction in one of the shim insertion cavities in the group that is explained as the second technique. Furthermore, in the above-described embodiments, an explanation is given of the technique for forming the cover for the insertion opening of the shim insertion cavity, the technique for connecting the shim housing boxes, or the like; however, they may be applied to the contents that are explained with reference to FIG. 12 to FIG. 16B.

With the magnetic resonance imaging apparatus and the gradient coil according to at least one of the above-described embodiments, it is possible to improve the efficiency of a shimming operation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
   a static field magnet configured to generate a static magnetic field within a substantially cylindrical hollow space;
   a substantially cylindrical gradient coil assembly disposed inside the static field magnet and configured to generate a gradient magnetic field, said gradient coil assembly including two spaced-apart substantially concentric cylindrical cooling layers sandwiching there-between a plurality of shim pocket insertion guide cavities extending axially between opposite ends of the gradient coil assembly; and
   a plurality of shim housing boxes, each being configured to house a plurality of metallic shims and sized such that an attractive force of the static magnetic field applied to one of the housing boxes containing a maximum possible number of shims becomes smaller than a predetermined threshold,
   wherein:
   a first plurality of said shim pocket insertion guide cavities have a first cross-sectional size and are located at first radial directional positions which are circumferentially distributed,
   a second plurality of said shim pocket insertion guide cavities have a second cross-sectional size and are located at second radial directional positions which are circumferentially distributed,
   said first cross-sectional size and said first radial directional positions being larger than said second cross-sectional size and said second radial directional positions respectively,
   on edge end surfaces of the gradient coil assembly, insertion openings of the shim pocket insertion guide cavities are provided, and
   the shim housing boxes include boxes sized to pass within said insertion openings and along respectively associated shim pocket insertion guide cavities having said first and second cross-sectional sizes, said shim housing boxes being configured to be inserted into one of the shim pocket insertion guide cavities through one of the insertion openings, the plurality of shim housing boxes being arranged side by side in multiple columns, in a radial direction of the substantially cylindrical hollow.

2. The magnetic resonance imaging apparatus according to claim 1, wherein:
   the shim housing boxes are configured to be sequentially inserted into one of the shim pocket insertion guide cavities through one of the insertion openings and becoming interconnected with one another without being previously interconnected to another shim housing box.

3. The magnetic resonance imaging apparatus according to claim 1, further comprising:
   a shim housing box cover and shim pressing mechanism for each shim housing box, said cover and shim pressing mechanism configured to be affixed to a respectively associated shim housing box and to fixedly contain one or more metallic shims under pressure there-within;

wherein:
the shim pocket insertion guide cavities are configured for an insertion of plural shim housing boxes through either of two insertion openings, one of said insertion openings being formed on each end of the shim pocket insertion guide cavities in the axial direction.

4. The magnetic resonance imaging apparatus according to claim 1, wherein:
the shim pocket insertion guide cavities each include a mechanism at an end portion operable to thereat easily attach and detach (a) one of the shim housing boxes placed at the end portion in the axial direction, or (b) a similarly sized replacement for one of the shim housing boxes placed at the end portion in the axial direction.

5. The magnetic resonance imaging apparatus according to claim 1, wherein each of a plurality of the shim housing boxes includes a convex portion centrally located on one of its side surfaces and a concave portion centrally located on an opposite one of its side surfaces, thereby making each of the plurality of shim housing boxes connectable to other of these so-configured shim housing boxes by linearly mating the convex and concave portions thereof using only axially directed relative motion.

6. The magnetic resonance imaging apparatus according to claim 1, wherein:
on each of circumferentially spaced multiple locations, a group of insertion openings of multiple shim pocket insertion guide cavities is provided, each said group being spaced from other of said groups.

7. The magnetic resonance imaging apparatus according to claim 6, wherein the shim pocket insertion guide cavities are formed such that the shim pocket insertion guide cavities are separated into multiple tiers and the shim housing boxes are configured to be inserted into a respectively corresponding tier of the shim pocket insertion guide cavities.

8. The magnetic resonance imaging apparatus according to claim 7, wherein the shim pocket insertion guide cavities are formed such that the shim pocket insertion guide cavities are separated into a first tier and a second tier that is a smaller tier compared to the first tier, said first and second tiers being radially spaced from each other.

9. The magnetic resonance imaging apparatus according to claim 1, wherein at least some of said shim pocket insertion guide cavities include a concave portion and a convex portion on one inner wall side, wherein the plurality of shim housing boxes is inserted into the shim pocket insertion guide cavity such that the plurality of shim housing boxes is in contact with the convex portion of the inner wall side while leaving an air layer within the concave portion on that same inner wall side thereby providing an adiabatic air layer suppressing changes in temperature of metallic shims contained within the shim housing boxes.

10. A magnetic resonance imaging apparatus comprising:
a static field magnet configured to generate a static magnetic field within a substantially cylindrical hollow space;
a substantially cylindrical gradient coil assembly being provided inside the static field magnet and configured to generate a gradient magnetic field, said gradient coil assembly including two spaced-apart substantially concentric cylindrical cooling layers sandwiching there-between a plurality of shim pocket insertion guide cavities extending axially between opposite ends of the gradient coil assembly; and
a plurality of shim housing boxes, each being configured to house a plurality of metallic shims,
wherein:
on an edge surface of the gradient coil assembly, insertion openings of the plurality of shim pocket insertion guide cavities penetrating through an entire length in a long axis direction are provided at multiple locations scattered in a circumferential direction,
a group of insertion openings of the shim pocket insertion guide cavities is provided at each of the multiple locations,
the plurality of shim housing boxes being configured for insertion into one of the shim pocket insertion guide cavities through one of the group of insertion openings, and
a plurality of the insertion openings is arranged in a radial direction of the substantially cylindrical hollow as the group of insertion openings.

11. A magnetic resonance imaging (MRI) gradient coil assembly comprising:
a plurality of shim housing boxes capable of housing plural metallic shims, wherein:
the plurality of shim housing boxes is formed into a shape such that an attractive force of an MRI static magnetic field applied to a shim housing box becomes smaller than a predetermined threshold,
wherein
a first plurality of shim pocket insertion guide cavities having a first cross-sectional size and located at first radial directional positions circumferentially distributed at an end of the gradient coil assembly,
a second plurality of guide cavities having a second cross-sectional size and located at second radial directional positions circumferentially distributed at an end of the gradient coil assembly,
said first cross-sectional size and said first radial directional positions being larger than said second cross-sectional size and said second radial directional positions respectively,
on an edge surface of the gradient coil assembly, insertion openings of a plurality of said shim pocket insertion guide cavities extending axially between opposite ends of the gradient coil assembly, and
the shim housing boxes including boxes sized to pass within said insertion openings and along respectively associated shim pocket insertion guide cavities having said first and second cross-sectional sizes, said shim housing boxes being configured to be inserted into one of the plurality of shim pocket insertion guide cavities through one of the insertion openings, the shim housing boxes when so inserted being arranged side by side in multiple columns, in a radial direction of a substantially cylindrical hollow within which an MRI static field magnet generates its static magnetic field.

12. The magnetic resonance imaging (MRI) gradient coil assembly according to claim 11 further comprising:
two spaced-apart substantially concentric cylindrical cooling layers sandwiching there-between the plurality of shim pocket insertion guide cavities.

* * * * *